(12) United States Patent
Newell et al.

(10) Patent No.: US 10,166,030 B2
(45) Date of Patent: Jan. 1, 2019

(54) SURGICAL TOOL SYSTEM HAVING MULTIPLE TOOL TIP INTERFACES

(71) Applicant: Modular Surgical, Inc., Los Altos, CA (US)

(72) Inventors: Matt Newell, Redwood City, CA (US); Luke Clauson, Redwood City, CA (US); Amir Belson, Los Altos, CA (US)

(73) Assignee: Modular Surgical, Inc., Los Altos, CA (US)

( * ) Notice: Subject to any disclaimer, the term of this patent is extended or adjusted under 35 U.S.C. 154(b) by 0 days.

(21) Appl. No.: 14/613,010

(22) Filed: Feb. 3, 2015

(65) Prior Publication Data

US 2015/0216515 A1    Aug. 6, 2015

Related U.S. Application Data

(60) Provisional application No. 61/935,227, filed on Feb. 3, 2014.

(51) Int. Cl.

| | |
|---|---|
| *A61B 17/00* | (2006.01) |
| *A61B 18/14* | (2006.01) |
| *A61B 17/16* | (2006.01) |
| *A61B 17/29* | (2006.01) |
| *A61B 17/3201* | (2006.01) |
| *A61B 17/32* | (2006.01) |

(Continued)

(52) U.S. Cl.
CPC .......... *A61B 17/1622* (2013.01); *A61B 17/29* (2013.01); *A61B 17/3201* (2013.01); *A61B 17/32002* (2013.01); *A61B 18/082* (2013.01); *A61B 18/1445* (2013.01); *A61B 90/361* (2016.02); *A61B 2017/00017* (2013.01); *A61B 2017/00022* (2013.01); *A61B 2017/00225* (2013.01); *A61B 2017/00283* (2013.01); *A61B 2017/00362* (2013.01); *A61B 2017/00398* (2013.01); *A61B 2017/00464* (2013.01); *A61B 2017/00473* (2013.01); *A61B 2017/00477* (2013.01); *A61B 2017/2931* (2013.01)

(58) Field of Classification Search
CPC ............ A61B 17/32002; A61B 17/29; A61B 18/1445; A61B 1/00101
USPC .......................................................... 606/1
See application file for complete search history.

(56) References Cited

U.S. PATENT DOCUMENTS

| | | |
|---|---|---|
| 5,925,002 A | 7/1999 | Wollman |
| 6,309,397 B1 | 10/2001 | Julian et al. |

(Continued)

FOREIGN PATENT DOCUMENTS

| | | | |
|---|---|---|---|
| WO | WO2010098871 | * 9/2010 | ............. A61B 17/32 |
| WO | WO-2013048963 A2 | 4/2013 | |

OTHER PUBLICATIONS

International search report and written opinion dated Jun. 26, 2015 for PCT/US2015/014316.

(Continued)

*Primary Examiner* — Scott T Luan
(74) *Attorney, Agent, or Firm* — Wilson Sonsini Goodrich & Rosati

(57) ABSTRACT

A surgical tool system includes a surgical tool shaft having a distal end and a proximal end. A plurality of surgical tool tips detachably connect to the distal end of the shaft. The surgical tool shaft includes a low power electrical interface, a high power electrical interface, and a mechanical interface.

8 Claims, 15 Drawing Sheets

(51) Int. Cl.
   *A61B 18/08*        (2006.01)
   *A61B 90/00*        (2016.01)

(56) References Cited

U.S. PATENT DOCUMENTS

| | | | |
|---|---|---|---|
| 7,492,116 B2 | 2/2009 | Oleynikov et al. | |
| 8,747,394 B2* | 6/2014 | Belson | A61B 17/00234 606/1 |
| 8,858,538 B2* | 10/2014 | Belson | A61B 17/00234 600/106 |
| 2003/0114731 A1 | 6/2003 | Cadeddu et al. | |
| 2005/0043718 A1 | 2/2005 | Madhani et al. | |
| 2005/0165449 A1 | 7/2005 | Cadeddu et al. | |
| 2005/0209607 A1 | 9/2005 | Lipchitz et al. | |
| 2006/0020287 A1* | 1/2006 | Lee | A61B 17/062 606/205 |
| 2006/0041273 A1 | 2/2006 | Ortiz et al. | |
| 2007/0198000 A1 | 8/2007 | Miyamoto et al. | |
| 2008/0021274 A1* | 1/2008 | Bayer | A61B 1/0008 600/112 |
| 2008/0108871 A1 | 5/2008 | Mohr | |
| 2008/0147096 A1 | 6/2008 | Aznoian et al. | |
| 2008/0167672 A1 | 7/2008 | Giordano et al. | |
| 2008/0275480 A1 | 11/2008 | Jacobs et al. | |
| 2009/0005638 A1 | 1/2009 | Zwolinski | |
| 2009/0182193 A1* | 7/2009 | Whitman | A61B 1/00101 600/104 |
| 2010/0016855 A1* | 1/2010 | Ramstein | A61B 1/00105 606/49 |
| 2010/0057078 A1 | 3/2010 | Arts et al. | |
| 2010/0188493 A1* | 7/2010 | Kanzaki | A61B 1/00059 348/75 |
| 2011/0087267 A1 | 4/2011 | Spivey et al. | |
| 2012/0083826 A1 | 4/2012 | Chao et al. | |
| 2012/0132450 A1 | 5/2012 | Timm et al. | |
| 2013/0066304 A1 | 3/2013 | Belson et al. | |
| 2013/0150871 A1 | 6/2013 | Belson et al. | |
| 2013/0211196 A1 | 8/2013 | Belson et al. | |

OTHER PUBLICATIONS

European Search Report and Search Opinion dated Dec. 8, 2017 for European Patent Application No. EP15743204.8.

* cited by examiner

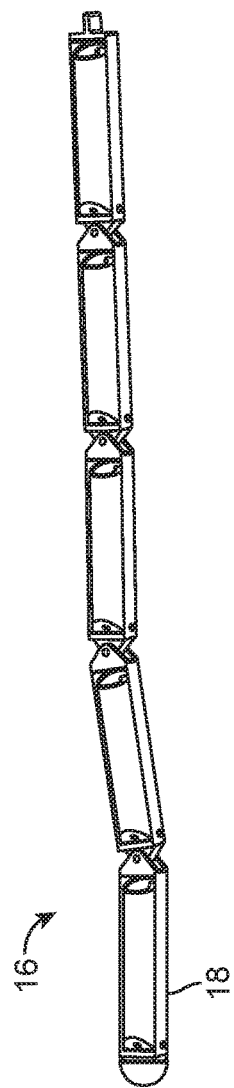
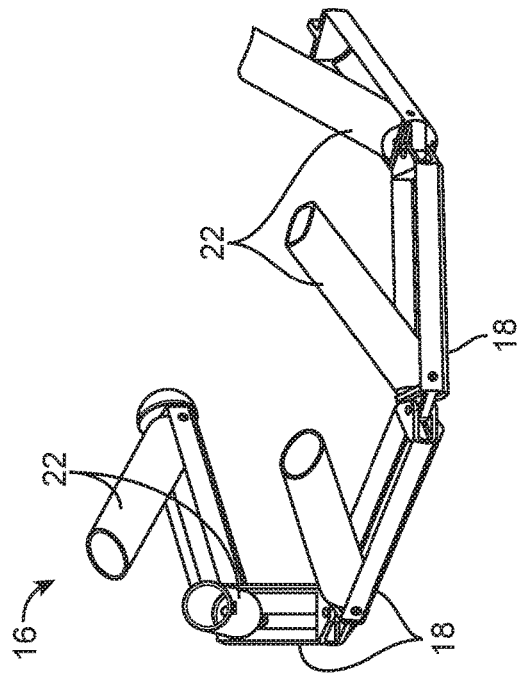
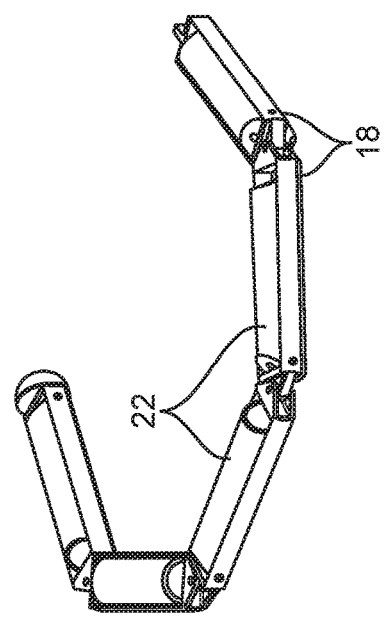
FIG. 7A
FIG. 7B
FIG. 7C

SURGICAL TOOL SYSTEM HAVING MULTIPLE TOOL TIP INTERFACES

CROSS-REFERENCE TO RELATED APPLICATIONS

The present application claims the benefit of U.S. Provisional Application 61/935,227, filed on Feb. 3, 2014, the full disclosure of which is incorporated herein by reference.

BACKGROUND OF THE INVENTION

1. Field of the Invention

The present invention relates generally to medical devices and methods. More particularly, the present invention relates to surgical tool systems for endoscopic and laparoscopic procedures where a single tool shaft can be used with multiple surgical tool tips.

Laparoscope and other endoscopic surgical procedures are widely used and have replaced many open surgical procedures. Laparoscopic procedures are performed within body cavities, such as the abdomen or thorax, and rely on introducing a shaft through a small incision, trocar or other access point through tissue which provide access into the cavity. In laparoscopic procedures, the shaft manipulates a tool or end effector to perform a surgical protocol while viewing the surgical field within the cavity using a camera. One drawback in performing laparoscopic and other endoscopic procedures is the need to frequently exchange tools through a limited number of access points.

It has been proposed to increase the efficiency of laparoscopic and other endoscopic procedures by introducing a plurality of surgical tool tips into the surgical field, such as an insufflated abdomen or thorax, and subsequently exchanging tools on a single or limited number of tool shafts, thus avoiding the need to remove and exchange complete tools through the access points. Such surgical tools exchange systems and procedures are described, for example, in commonly owned U.S. Patent Publication No. 2013/0150871, the full disclosure which is incorporated herein by reference.

2. Background Art

U.S. Patent Publication 2013/0150871 has been described above. See also U.S. Pat. Nos. 5,925,002; 6,309,397; and 7,492,116; as well as U.S. Publication Nos. 2003/0114731; 2005/0043718; U.S. 2005/0209607; U.S. 2006/0041273; U.S. 2007/0198000; U.S. 2008/0108871; U.S. 2008/0147096; US. 2008/0167672; U.S. 2008/0275480; U.S 2009/0005638; and U.S. 2013/0066304.

SUMMARY OF THE INVENTION

In a first aspect, the present invention provides a surgical tool system comprising a surgical tool shaft having a distal end and proximal end. The surgical tool shaft includes a low power electrical interface, a high power electrical interface, and a mechanical interface. The system further comprises a plurality of surgical tools tips, wherein individual tool tips are detachably connectable to the distal end of the shaft. The individual tool tips will also include at least one of a low power electrical interface, a high power electrical interface, and a mechanical interface, wherein the interfaces on the tool tips are disposed on the tools so that they will mate with the corresponding interface on the shaft when the tool tip is mounted on the shaft. The low power electrical interface may provide power to sensors on the tool tip and/or receives data or other low power information from the tool tip. Alternatively, the low power electrical interface may provide control information to motors on the tool tip and/or receive control data or other low power information from the tool tip. The high power electrical interface will typically drive motors, power illumination, power cautery, power electrosurgical tools, or the like on the tool tip, while the mechanical interface will typically allow conventional grips, levers, or other manual drivers on the shaft or an associated handle to mechanically drive jaws, scissors, or the like on the tool tips.

In a first embodiment, at least some of the surgical tool tips have sensors which connect to the low power electrical interface. Sensors may comprise temperature sensors, environmental sensors, diagnostics sensors, and the like. In the second embodiment, at least some of the surgical tool tips may have cameras which connect to the low power electrical interface. In a third embodiment, at least some of the surgical tool tips may have electrodes which connect to the high power electrical interface, such as radiofrequency electrodes for performing electrosurgery and/or electrocautery. The electrodes may also comprise resistance heaters, ablation elements, cutting elements, and the like. In a fourth embodiment, at least some of the surgical tool tips will comprise electrical motors which connect to the high power electrical interface and optionally to the low power electrical interface as well for control and other purposes. Electric motors can be connected to the high and/or the low power interface and may drive tools or may be connected to cameras for adjusting focus or magnification. In a sixth embodiment, the mechanical interface will provide linear actuation for a tool on the surgical tip, such as for driving scissors, forceps, or other pivoted elements. In an eighth embodiment the mechanical interface will provide rotational actuation to drive, for example, drills, burrs, abrading elements, and the like. In some arrangements, the mechanical interface may provide both rotational and linear actuation for selective connection to any of the end effectors described above for either or both rotational and linear actuation.

In a second aspect of the present invention, a tool system comprises a surgical tool shaft have a distal and a proximal end. A surgical tool tip is detachably connectable to the distal end of the shaft, and the tool shaft includes a surface feature which mates with a lock mechanism on the tool tip so that rotation of the shaft relative to the tool tip releases the tip from the a holding member. For example, a shaft may have a cylindrical outer surface and the surface feature may comprise at least one flat face or facet on the cylindrical surface which engages a cam or other similar mechanism in the surgical tool tip to cause release of the tip from the holder.

In a third aspect of the present invention, a tool tip cassette system comprises a tool carrier including a plurality of tool carrier segments at least some of which are connected with articulating joints. The terms "cassette" and "carrier" will be used interchangeably herein and in the claims. The cassette system further comprises a cassette manipulator including a handle and an attachment shaft. The shaft is configured to pass through tissue from an external location, typically through a cannula or a direct incision in the tissue, to a location in the body cavity. A distal end of the attachment shaft is configured to be detachably secured to the tool carrier while the tool carrier is within the body cavity. A handle is usually attached to the shaft at the external location and can be used to manipulate the tool carrier segments, for example by pulling the segments against an inner wall of a patient's thorax. Typically, the cassette manipulator will include a mechanism to selectively release the tool carrier from the shaft/or to selectively to release the manipulator from the shaft. In still other embodiments, the manipulator may provide mechanisms on the handle which allow the physician to reconfigure the tool carrier segments within the body cavity, for example, by straightening or bending the carrier segments, by releasing individual tool holders from each segments to make the circle tool tips accessible, or the like.

BRIEF DESCRIPTION OF THE DRAWINGS

FIGS. 7A-7C illustrate the straight, deployed, and the tool holder deployed configurations of the tool tip cassette system of the present invention.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Figure 1:
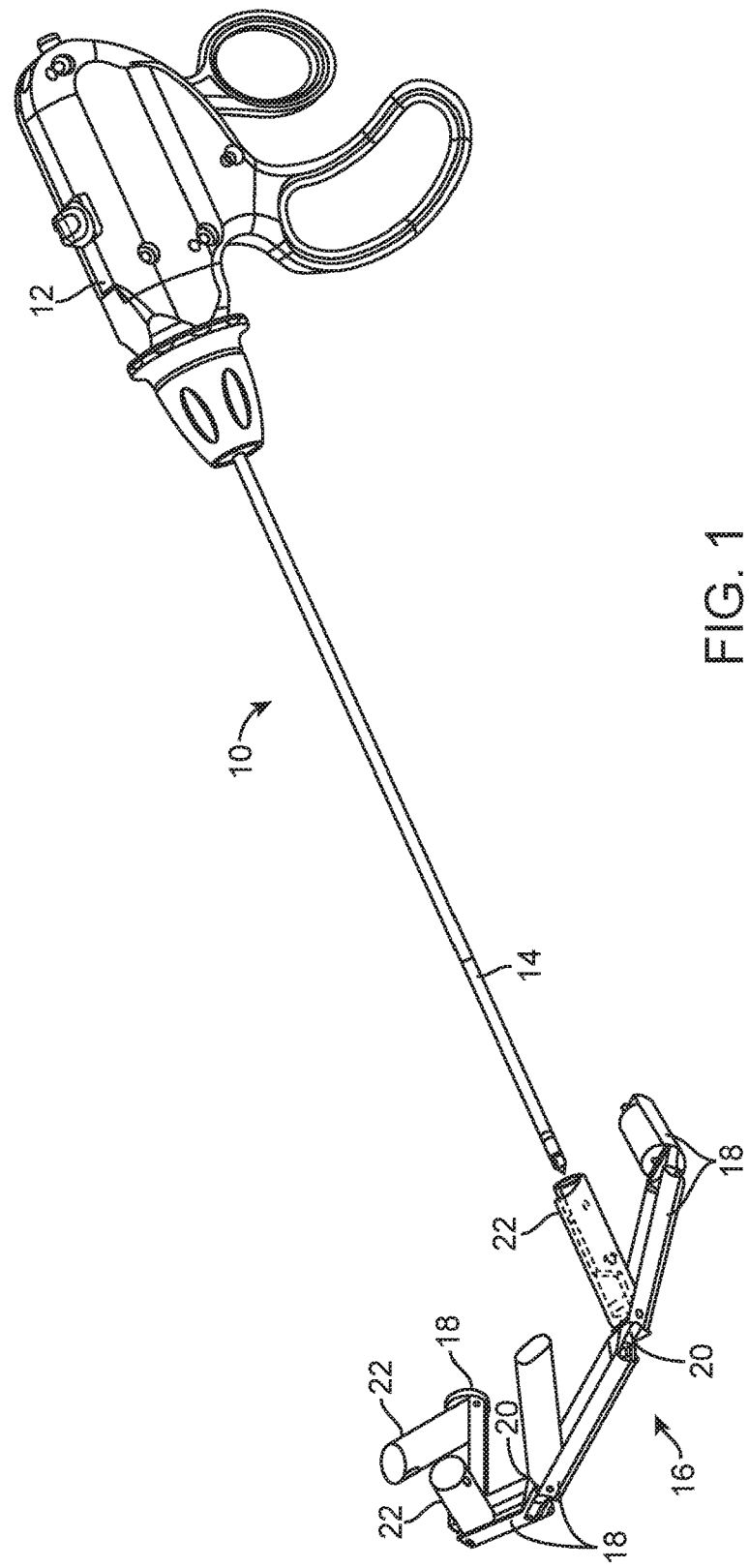
FIG. 1 illustrates a surgical tool system and a tool tip cassette system constructed in accordance with the principles of the present invention.

FIG. 1 illustrates a complete tool system with cassette. The tool system 10 includes a handle 12 and shaft 14. A cassette system 16 includes a plurality of individual segments 18 with articulating joints 20 and deployable tool holders 22, each of which cradles a removable surgical tool tip 36 (FIG. 2).

Figure 2:
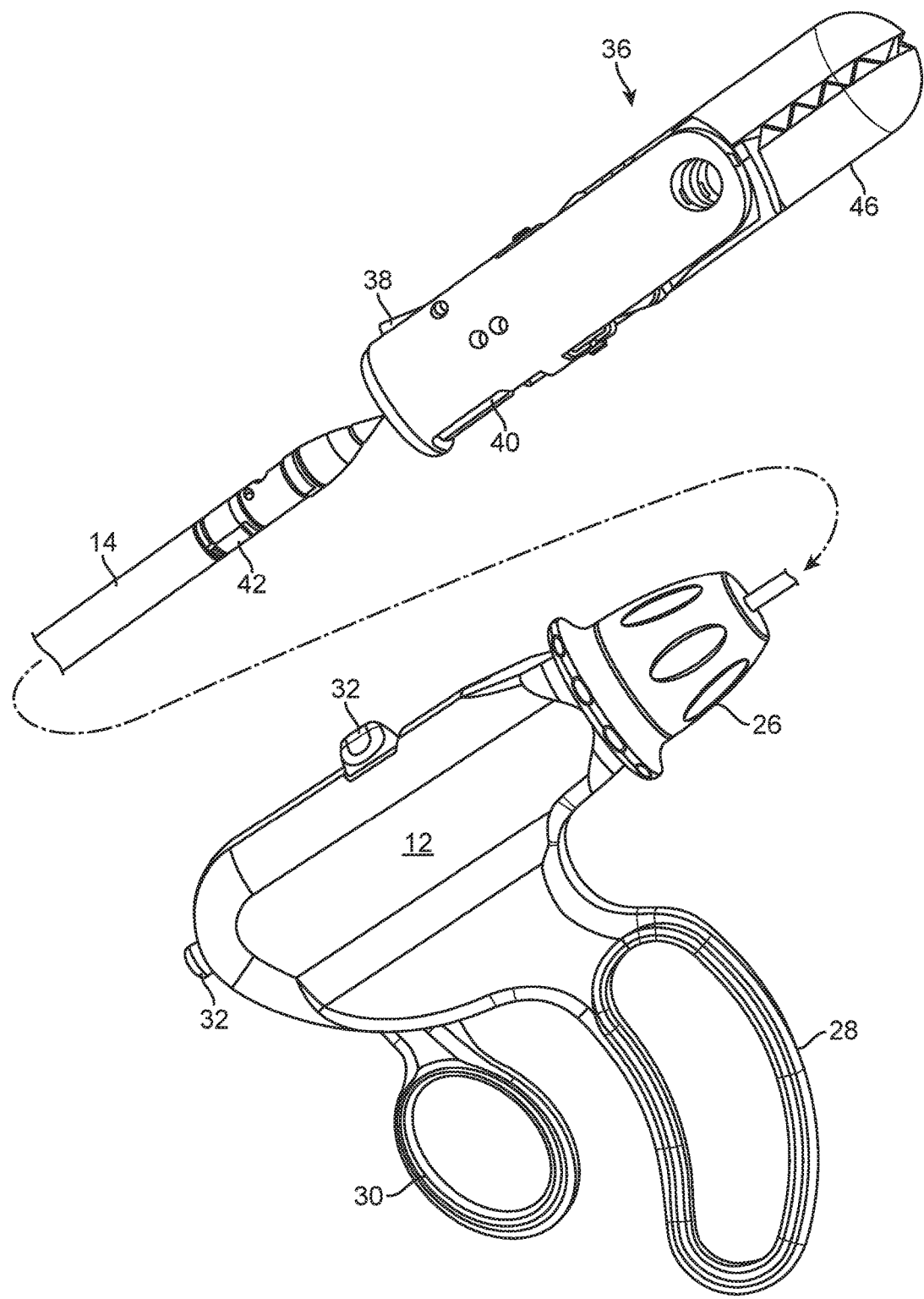
FIG. 2 illustrates a surgical tool shaft as being introduced to a surgical tool tip.

The tool system 10 is shown in more detail in FIG. 2. The handle 12 includes a shaft rotator 26, a fixed finger grip 28 and a thumb actuator 30. The handle 12 typically house motors, controllers, and other components for driving and interfacing with the individual tool tips 36. The thumb actuator 30 will typically be connected to manipulate the tools in some desired way, for example, by mechanically opening and closing scissors, forceps, or other tool elements. Alternatively, the thumb actuator could actuate an electric motor to rotate the tool element, such as a burr, drill, or the like. Other features on the handle include a trocar button 32 and a trocar mode selector 34.

The shaft 14 of the tool system will typically (but not necessarily) have a pointed, electrosurgical, or other tissue-penetrating tip to allow direct introduction through tissue, i.e. not through a previously placed cannula. While not necessary, such shafts with tissue-penetrating element could be introduced through cannulas or pre-formed incisions.

An exemplary surgical tool tip 36 comprises a cassette-locking element, such as pawl 38, a printed circuit board or other low power electrical interface 40, and the like. A second or mating low power interface 42 will typically be provided on the shaft 14 in order to interconnect with the interface 40 on the tool. The tool 36 itself may comprise mechanical elements such as jaws 46, although other mechanical and non-mechanical end effectors may also be provided, such as electrodes, drills, cameras, electrodes, and the like.

Figure 3:
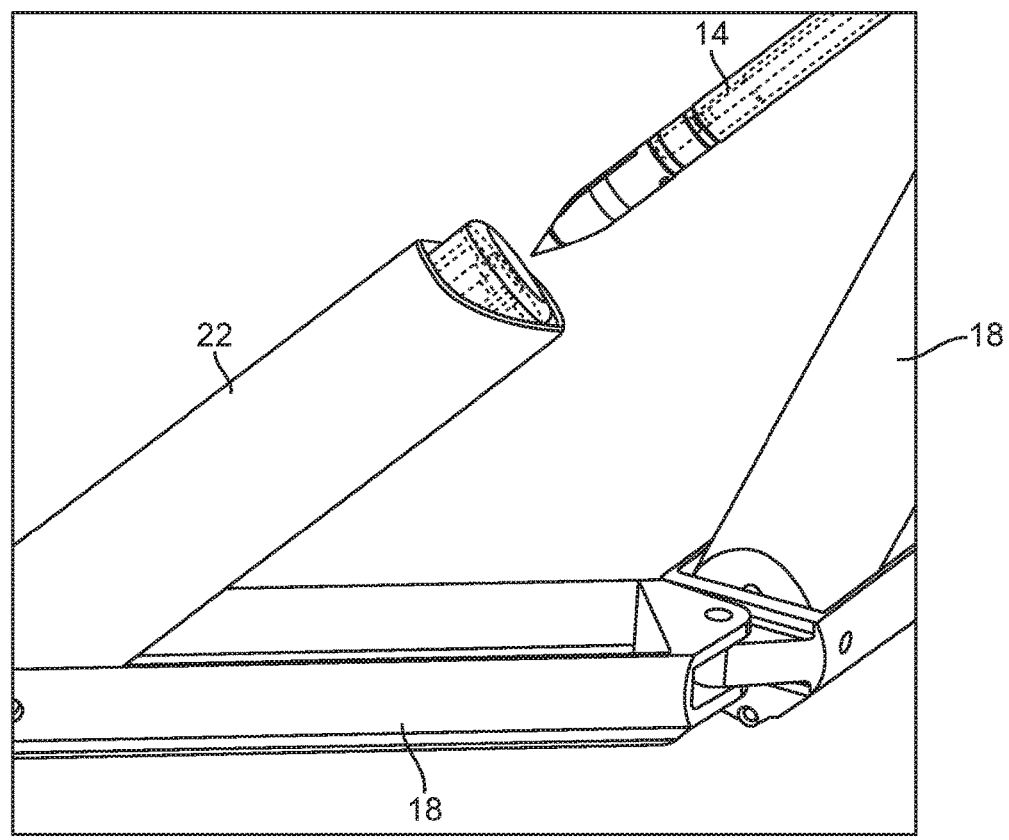
FIG. 3 is a detailed view of the surgical tool shaft entering a surgical tool tip while the tool tip is retained within a holding unit within the tool tip cassette system.

FIG. 3 provides a detailed view of the distal end of the shaft entering the tool 36 while it is held within a deployed tool holder 22 which is part of the cassette system 16. The tool holder is raised from a bay in the segment 18, and the distal end of the shaft 14, which is typically less than 3 mm in outside diameter, may be introduced into a larger or full sized tool tip, typically 8 mm, and thereafter may be locked onto the shaft, typically by the paw 38 (FIG. 2).

Figure 4A:
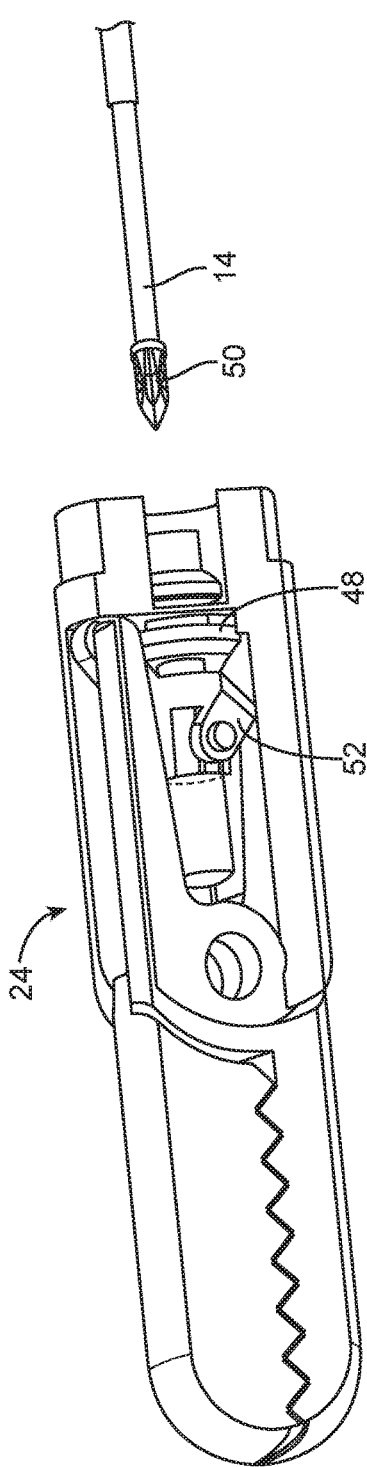
FIGS. 4A-4C illustrate in detail a distal end of the surgical tool shaft being introduced into a surgical tool tip.

FIG. 4A shows the distal end of the shaft 14 being introduced the surgical tool tip 36 where a rotational motion can drive the tool, such as graspers, cutters, camera zoom/focus, morcellator, or the like. Rotational motion is converted by a thrust bearing 48 where splines 50 on the tool tip engage a rotational mechanism to convert rotational motion into liner motion via a lever 52.

Figure 4B:
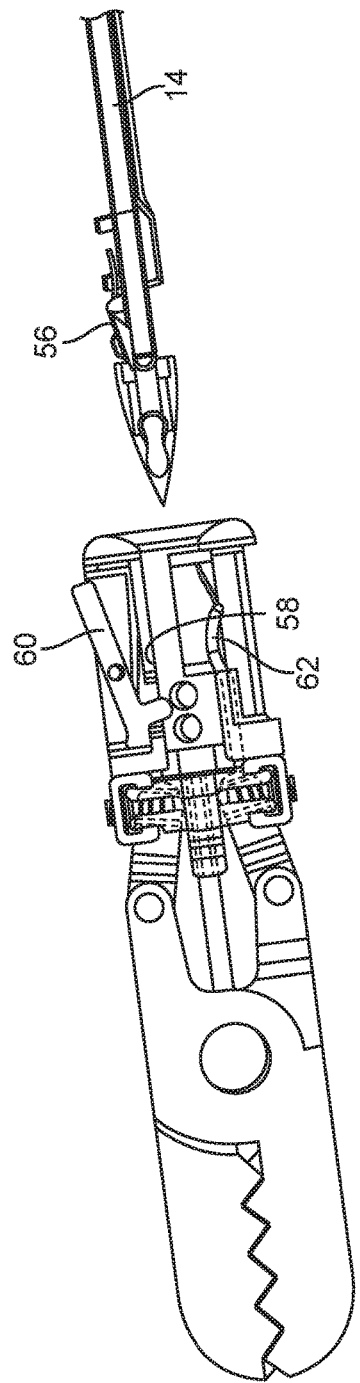
Figure 4C:
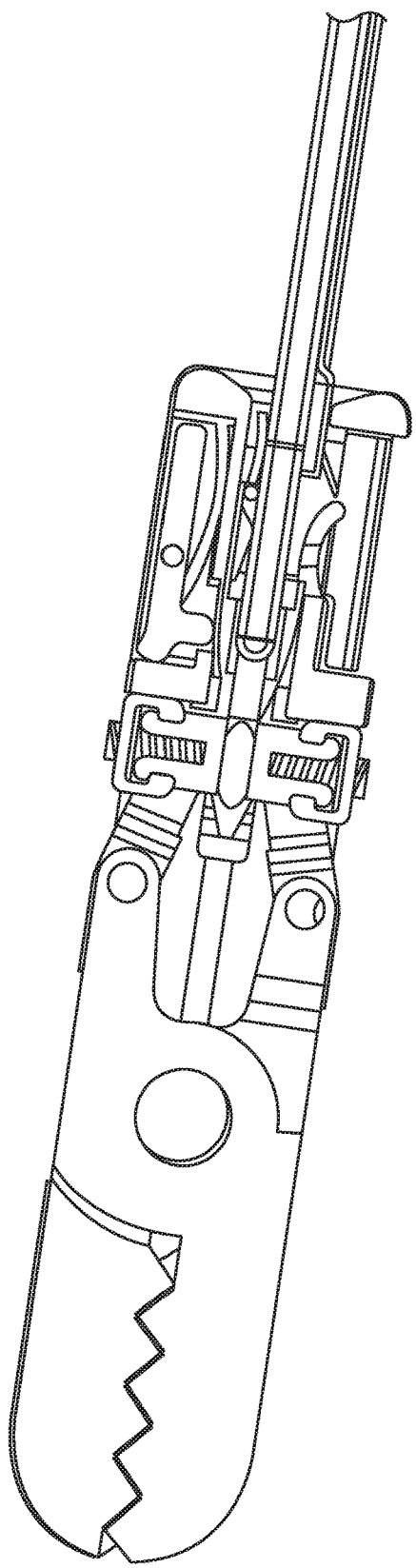

FIGS. 4B and 4C shows an alternative construction of the tool tip 36' and the distal end of shaft 14' with a collet leaf 56 (retracted in FIG. 4B and exposed in FIG. 4C) which is received into a collet leaf cavity 58 for locking and releasing the tool tip into a tool holder by canting latch element 60. A rotational alignment detent 62 is also provided. FIG. 4B shows the shaft 14' prior to insertion into tool 36', and FIG. 4C shows the shaft inserted into the tool.

Figure 5A:
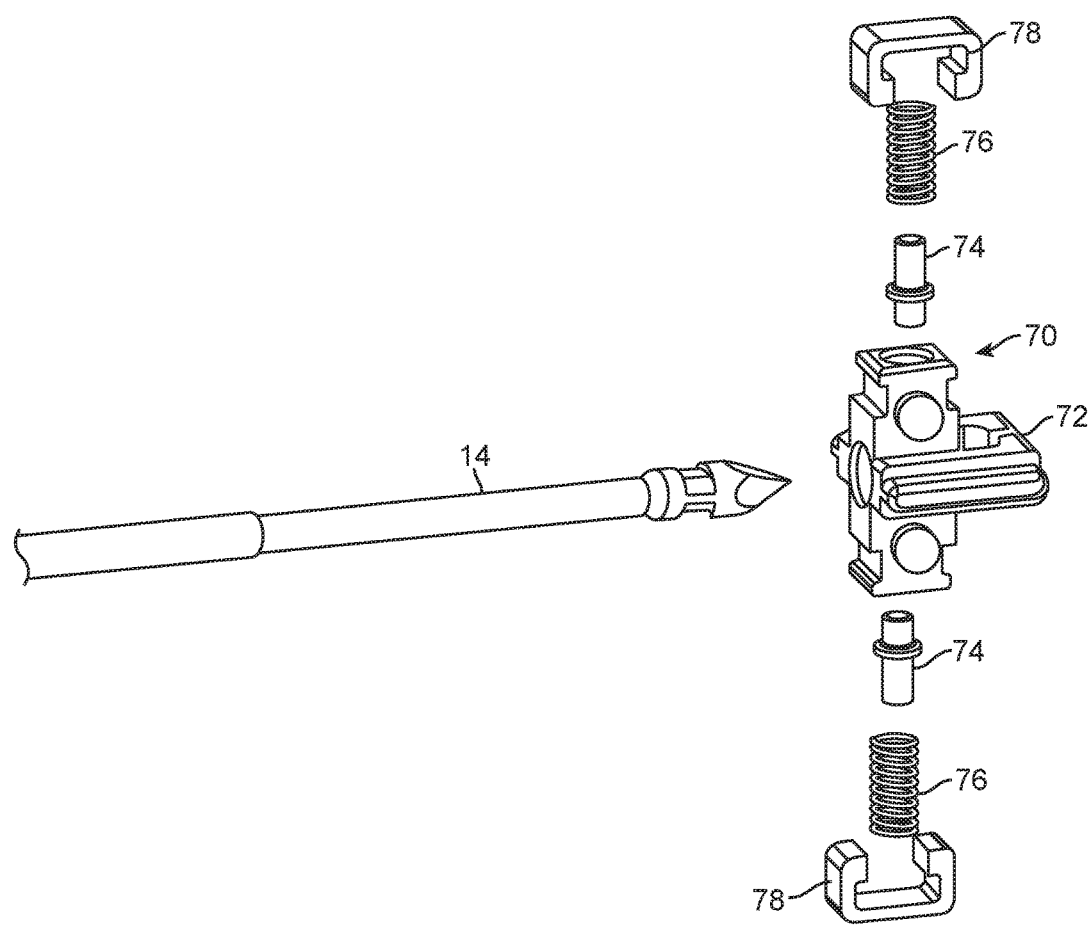
FIGS. 5A-5D illustrate details of the locking mechanism which allows the distal end of the surgical tool shaft to be rotated in order to release the shaft from the tool tip.
Figure 5B:
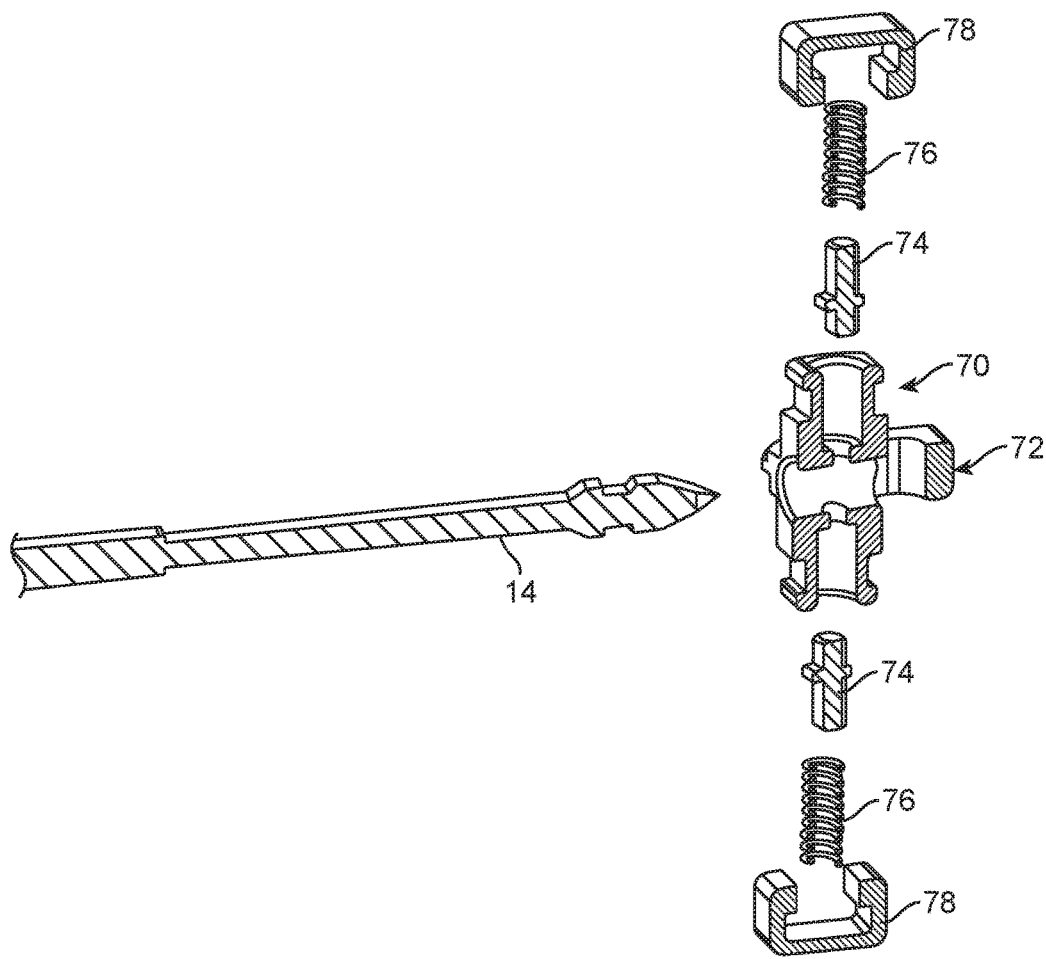
Figure 5C:
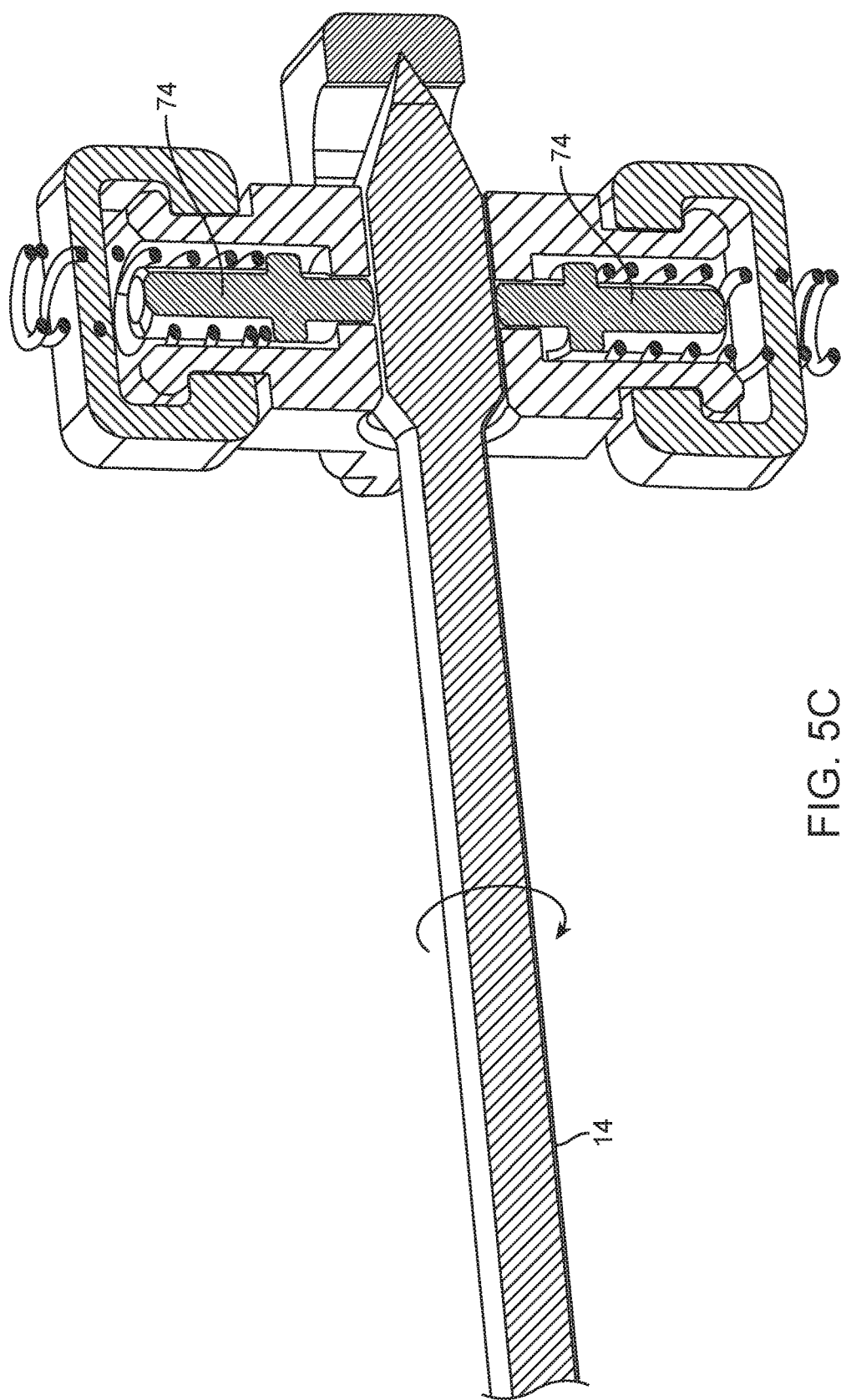
Figure 5D:
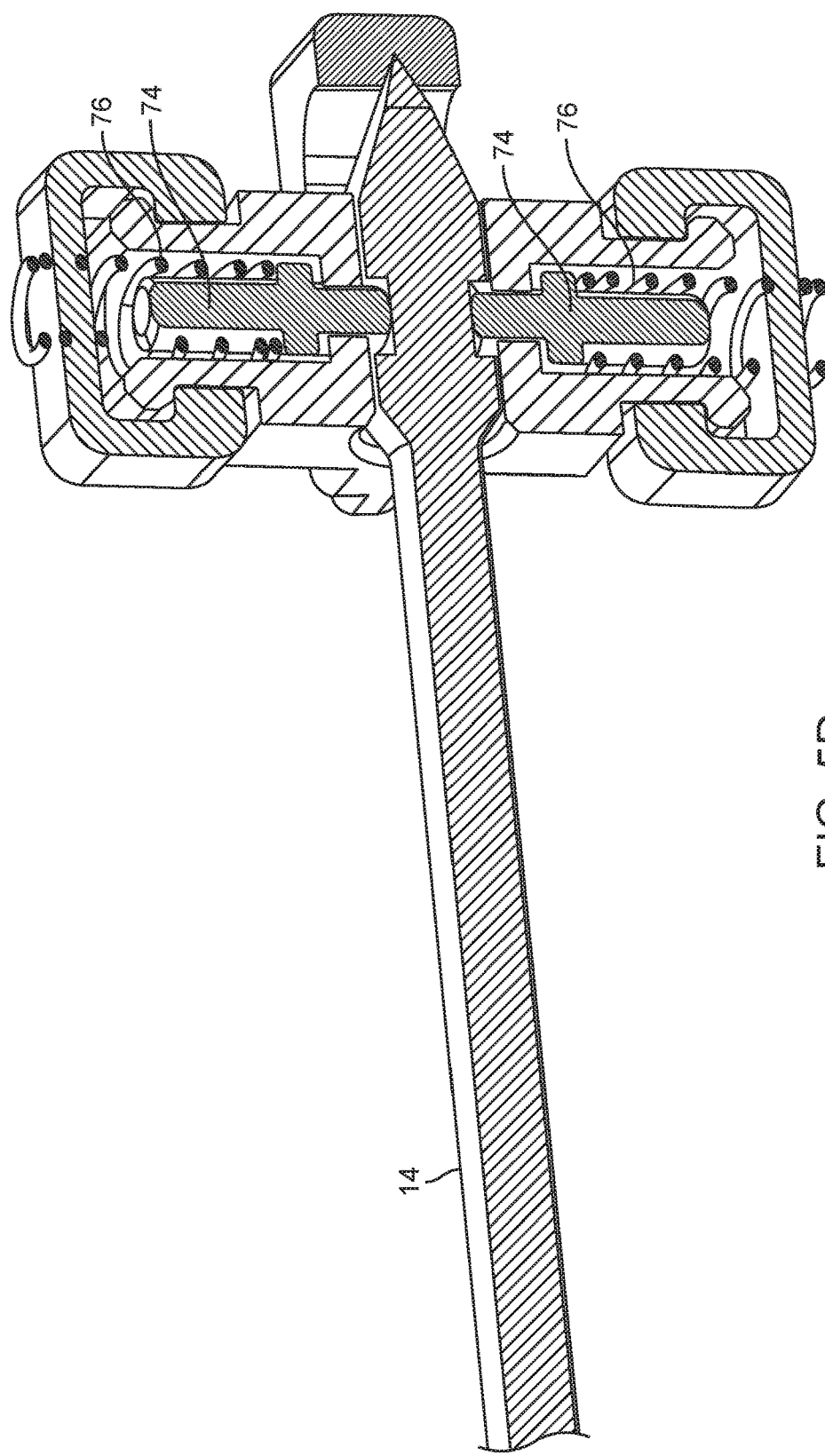

Details of the mechanism for locking and unlocking the shaft 14' into the surgical tool tip 36' are provided in FIGS. 5A-4D. Exploded views are shown in FIGS. 5A and 5B where a lock pin carrier 70 includes a trocar push off feature 72, lock tip 74, spring 76 and spring caps 78. An unlocked configuration is shown in FIG. 5C and a locked configuration is shown in FIG. 5D. By rotating the shaft 14 through 90°, as indicated by the arrow in FIG. 5C, flat facets or surfaces on the cylindrical face of the distal end of the shaft 14 allow the lock pins 74 to drop under the force of springs 76, allowing the spring caps 78 to disengage the locking lever.

Figure 6:
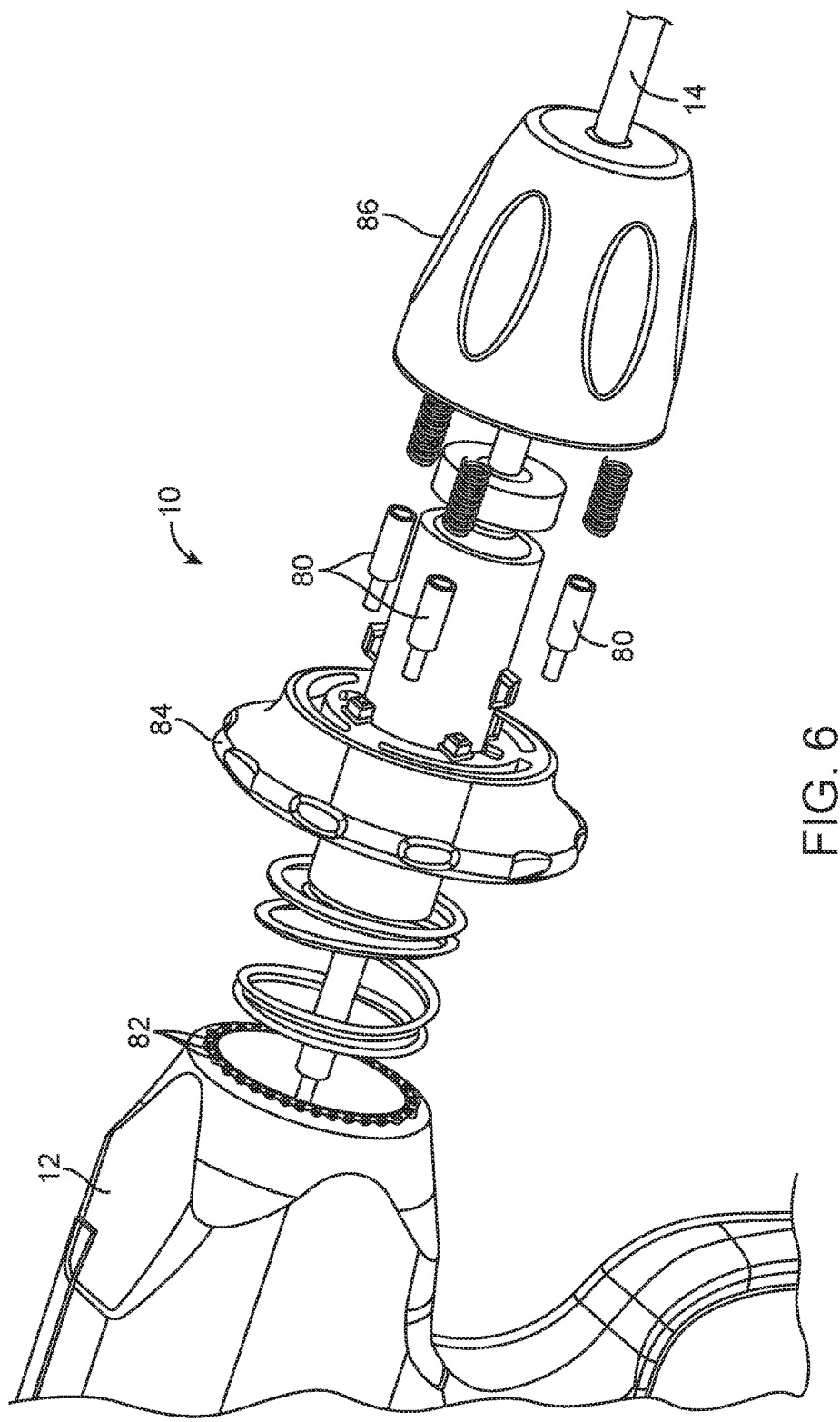
FIG. 6 illustrates the detailed construction of a proximal end of the surgical tool shaft where it is connected to a handle.

FIG. 6 illustrates an exploded view of the connection of the handle 12 of the tool system 10 to the shaft 14. Grounding pins 80 are movably received into grounding pin pockets 82, and a handle collar 84 may be pushed forward to disengage the grounding pins or be pulled back to engage the grounding pins, thus allowing a nose cone 86 to be selectively rotated. This allows the 90° rotation which is used for locking and unlocking the tool tip to the shaft of the device.

Figure 7:
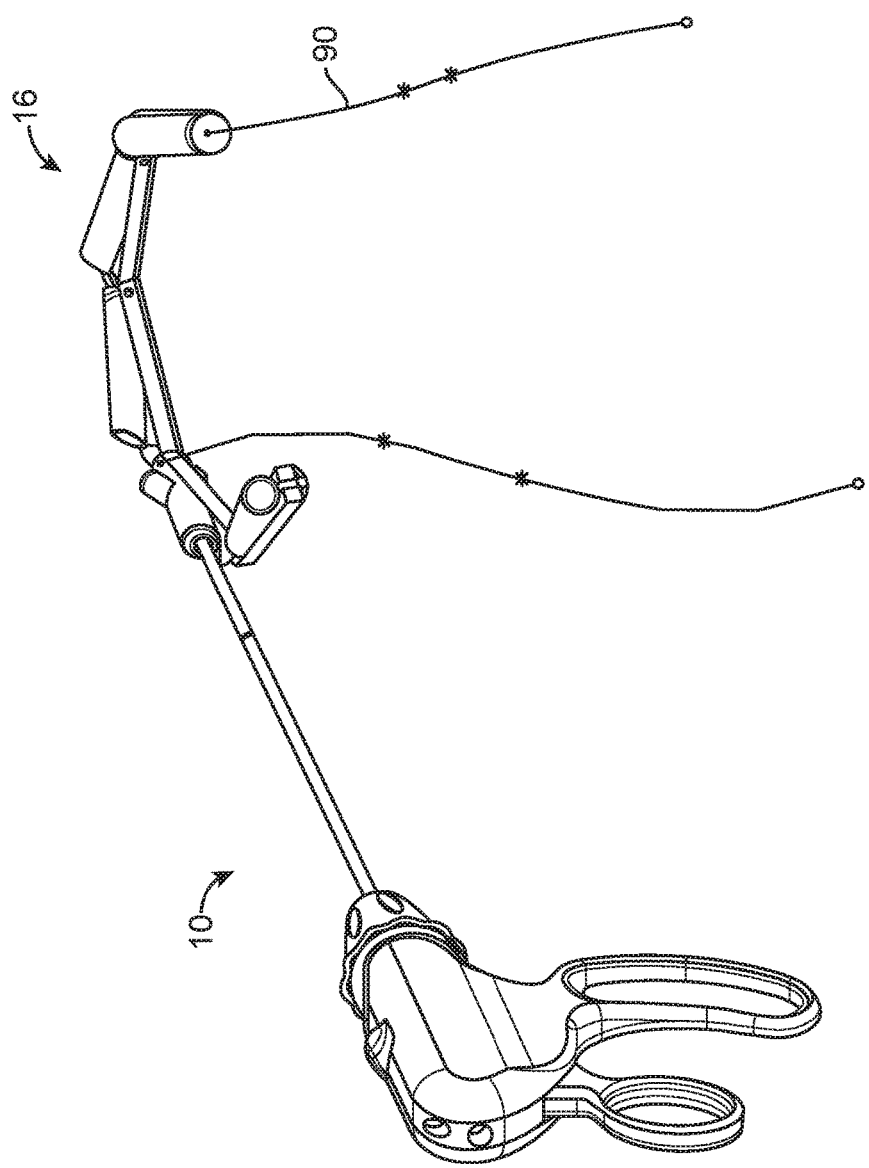
FIG. 7 illustrates the surgical tool system engaging a surgical tool tip held in a deployed tool tip cassette system.

FIG. 7 illustrates the tool system 10 and cassette system 16, where the cassette system 16 may be sutured in place with suture 90.

FIGS. 7A-7C illustrate various configurations of the tool cassette system 16. A linear configuration is shown in FIG.

7A. The linear configuration is typically used for introducing the cassette into the patient. For thoracoscopic procedures, the individual segments 18 and tools 36 may have non-circular cross sections in order to minimize the need to distract adjacent ribs for introduction. The tool cassettes are shown in their stable, curved configuration in 7B and further shown with individual tool holders 22 deployed in FIG. 7C.

Figure 8:
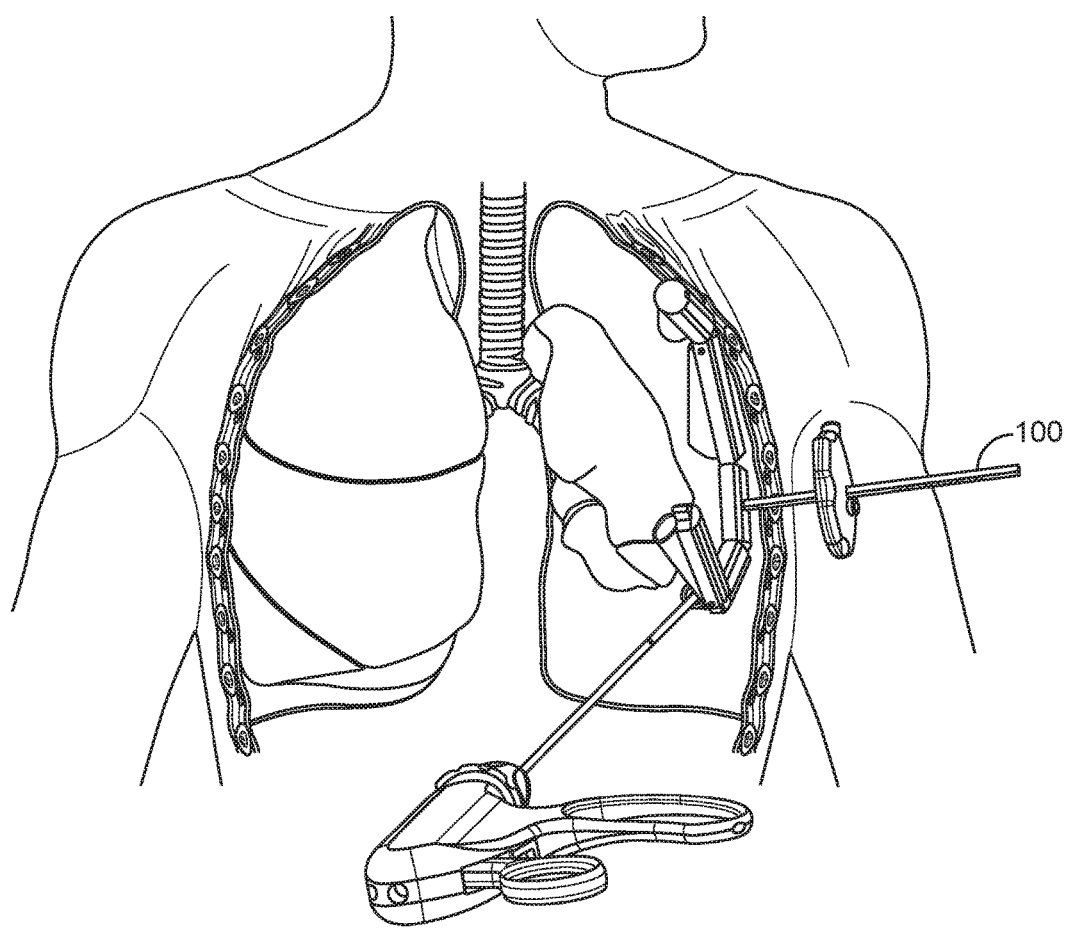
FIG. 8 illustrates the tool tip cassette system manipulator being used in a patient.
Figure 9:
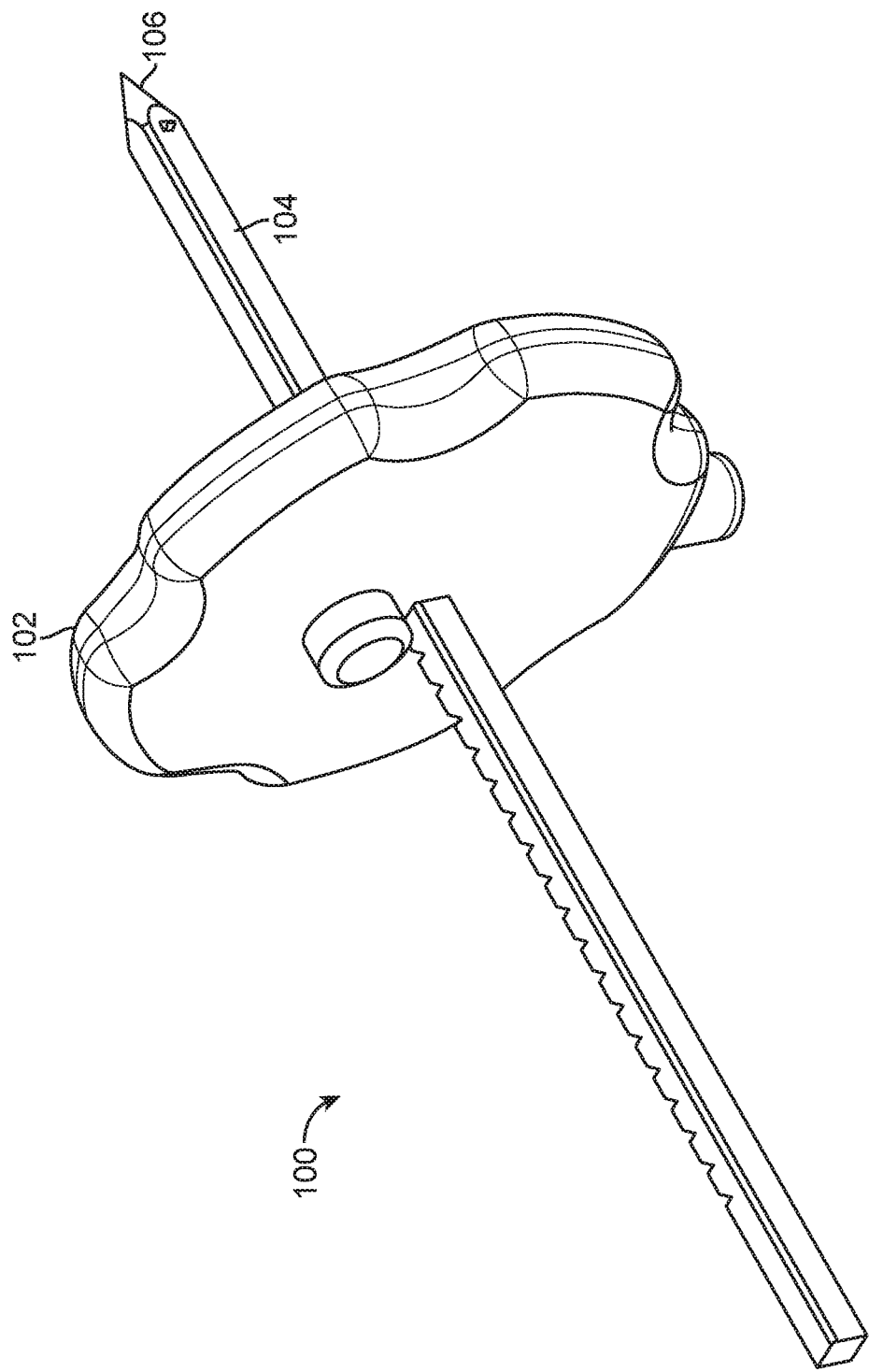
FIG. 9 illustrates the surgical tool manipulator prior to the attachment to a tool cassette.
Figure 10B:
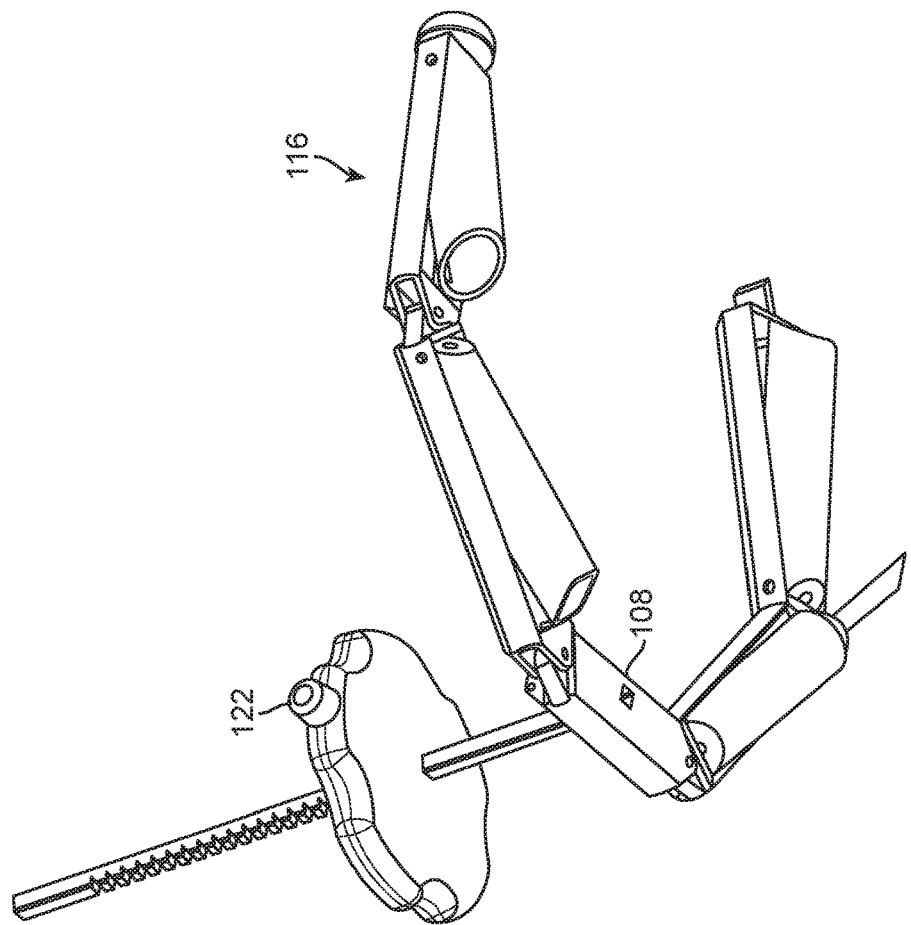
FIGS. 10A-10B illustrate the surgical tool manipulator of the present invention attached to a deployed tool cassette system.
Figure 10A:
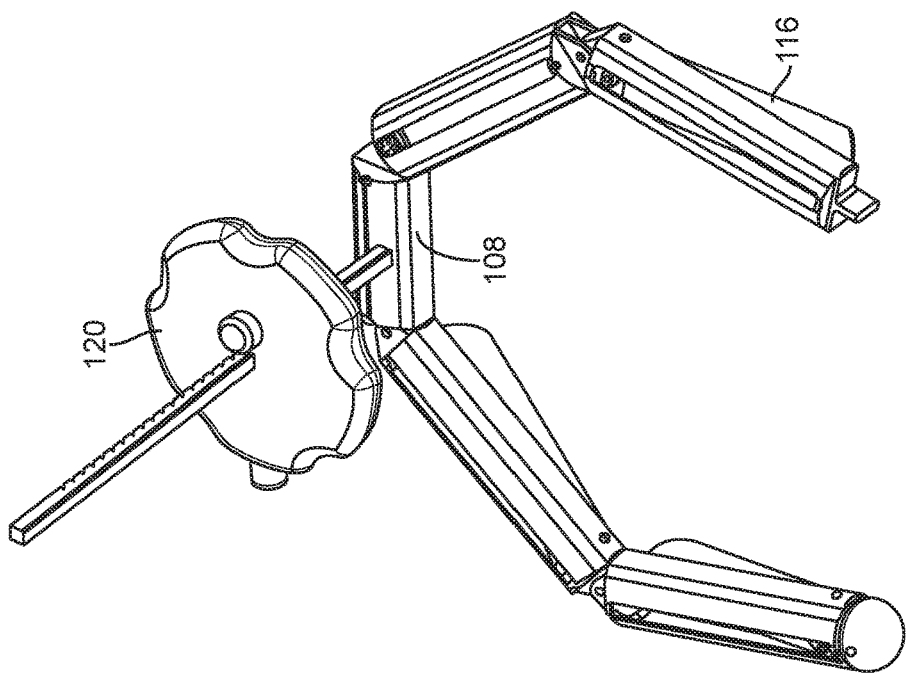

Referring now to FIG. 8, a cassette manipulator 100 is shown attached to a center segment of a tool cassette deployed in the thorax of a patient. As better seen in FIGS. 9 and 10A-10B, the cassette manipulator 100 includes a handle 102 and a shaft 104 where a distal tip 106 of the shaft can be detachably removed into a center segment 108 of the tool cassette system 116. The center segment 108 will typically not carry a tool and be provided as an interface for the shaft 104. After the tool cassette has been introduced into the thorax of the patient, as shown in FIG. 8, the shaft 104 may be transcutaneously introduced, typically using the sharpened or otherwise tissue-penetrating tip 106, and then engaged into the segment 108. The handle 102 can then be used to pull the cassette upwardly against the inner wall of the thorax, and the handle then ratcheted down against the outer skin of the patient in order to hold the tool cassette in place. At the end of the procedure, a release button 120 can be pressed to release the cassette. A second release button 122 is provided to disengage the ratchet which holds the handle in place while a tip to the shaft.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A tool tip carrier system comprising:
  a tool carrier including a plurality of tool carrier segments at least some of which are connected with articulating joints, wherein each tool carrier segment is configured to cradle a removable surgical tool tip; and
  a tool carrier manipulator including (i) a handle and (ii) an attachment shaft, wherein the handle is adjustably connected to be selectively positioned along a length of the attachment shaft;
  wherein the attachment shaft has a tissue-penetration tip which is configured to pass through tissue from an external location to a location in a body cavity and wherein a distal end of the attachment shaft is configured to be detachably secured to the tool carrier within the body cavity while the handle is attached to the shaft at the external location.

2. A tool tip carrier system as in claim 1, wherein the carrier manipulator includes a mechanism to selectively release the tool carrier from the shaft.

3. A tool tip carrier system as in claim 1, wherein the carrier manipulator includes a mechanism to selectively release the manipulator from the shaft.

4. A tool tip carrier system as in claim 1, wherein the handle is adjustably attached to the shaft by a ratchet.

5. A tool tip carrier system as in claim 4, wherein the ratchet is configured to allow the tool carrier to be pulled toward the handle as the handle is pressed down against the patient's outer skin.

6. A tool tip carrier system as in claim 5, wherein the handle comprises a first release button configured to release the tool carrier.

7. A tool tip carrier system as in claim 6, wherein the handle comprises a second release button configured to disengage the ratchet.

8. A tool tip carrier system as in claim 6, wherein the tool carrier includes a center segment which does not carry a tool and is configured as an interface to detachably receive the distal end of the attachment shaft.

* * * * *